United States Patent [19]
Wohlleben et al.

[11] Patent Number: 5,336,607
[45] Date of Patent: Aug. 9, 1994

[54] REGULATED GENE EXPRESSION IN STREPTOMYCETES

[75] Inventors: Wolfgang Wohlleben, Bielefeld; Günter Muth, Enger; Alfred Pühler, Bielefeld; Günther J. Rieb, Frankfurt am Main, all of Fed. Rep. of Germany

[73] Assignee: Hoechst Aktiengesellschaft, Frankfurt am Main, Fed. Rep. of Germany

[21] Appl. No.: 95,481

[22] Filed: Jul. 23, 1993

Related U.S. Application Data

[63] Continuation of Ser. No. 683,062, Apr. 10, 1991, abandoned.

[30] Foreign Application Priority Data

Apr. 12, 1990 [DE] Fed. Rep. of Germany ....... 4011863

[51] Int. Cl.5 ................... C12N 15/74; C12N 15/63
[52] U.S. Cl. ............... 435/172.3; 435/320.1; 536/23.7; 536/24.1
[58] Field of Search .......... 435/172.3, 69.1, 320.1; 536/23.7, 24.1

[56] References Cited

PUBLICATIONS

K. J. Kendall and S. N. Cohen, J. Bacteriol., 169:4177–83 (1987).
K. J. Kendall and S. N. Cohen, J. Bacteriol., 170:4634–51 (1988).
Stein et al. (Nov. 1989), J. Bacteriol., vol. 171 (11), pp. 5768–5775.
Birch et al. (Jun. 1985), J. Gen. Microbiol., vol. 131, pp. 1299–1303.
Schupp et al. (Apr. 29, 1988), Gene, vol. 64, pp. 179–188.

*Primary Examiner*—Richard A. Schwartz
*Assistant Examiner*—Philip W. Carter
*Attorney, Agent, or Firm*—Finnegan, Henderson Farabow, Garrett & Dunner

[57] ABSTRACT

The kil-kor system from the plasmid pIJ101 can be utilized for regulated gene expression in Streptomycetes. For this, the KorA protein is either inactivated or eliminated to "switch on" a particular gene.

1 Claim, 1 Drawing Sheet

SEQUENCE LISTING ( 1 ) GENERAL INFORMATION:

( i i i ) NUMBER OF SEQUENCES: 3

(2) INFORMATION FOR SEQ ID NO:1:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other
        (A) DESCRIPTION: Synthetic DNA (xi) SEQUENCE DESCRIPTION: SEQ ID NO:1:

```
CGCGTACGGG CACTTCGACT TGCGGCGCTG GTGGGTGCGG GCGCCGCACT CGCCCTGTCT    60

CCCCTCGC                                                             68
```

(2) INFORMATION FOR SEQ ID NO:2:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: Other
        (A) DESCRIPTION: Synthetic DNA (v) FRAGMENT TYPE: N-terminal (xi) SEQUENCE DESCRIPTION: SEQ ID NO:2:

```
GTACGCGCAT GCCCGTGAAG CTGAACGCCG CGACCACCCA CGCCCGCGGC GTGAGCGGGA    60

CAGAGGGGAG CGCCGG                                                    76
```

(2) INFORMATION FOR SEQ ID NO:3:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met  Arg  Val  Arg  Ala  Leu  Arg  Leu  Ala  Ala  Leu  Val  Gly  Ala  Gly  Ala
 1             5                        10                            15

Ala  Leu  Ala  Leu  Ser  Pro  Leu  Ala  Ala
              20                       25
```

REGULATED GENE EXPRESSION IN STREPTOMYCETES

This application is a continuation of application Ser. No. 07/683,062, filed Apr. 10, 1991, now abandoned.

BACKGROUND OF THE INVENTION

Although the Streptomycetes are among the most important producers of antibiotics, there is still relatively little known in relation to genetics. Thus, there is still little known about the mechanisms which control gene expression in Streptomycetes.

Although induced expression by thiostrepton is known, this is unsuitable for practical use on an industrial scale because of the high price and the low solubility in water.

SUMMARY OF THE INVENTION

Figure 1:
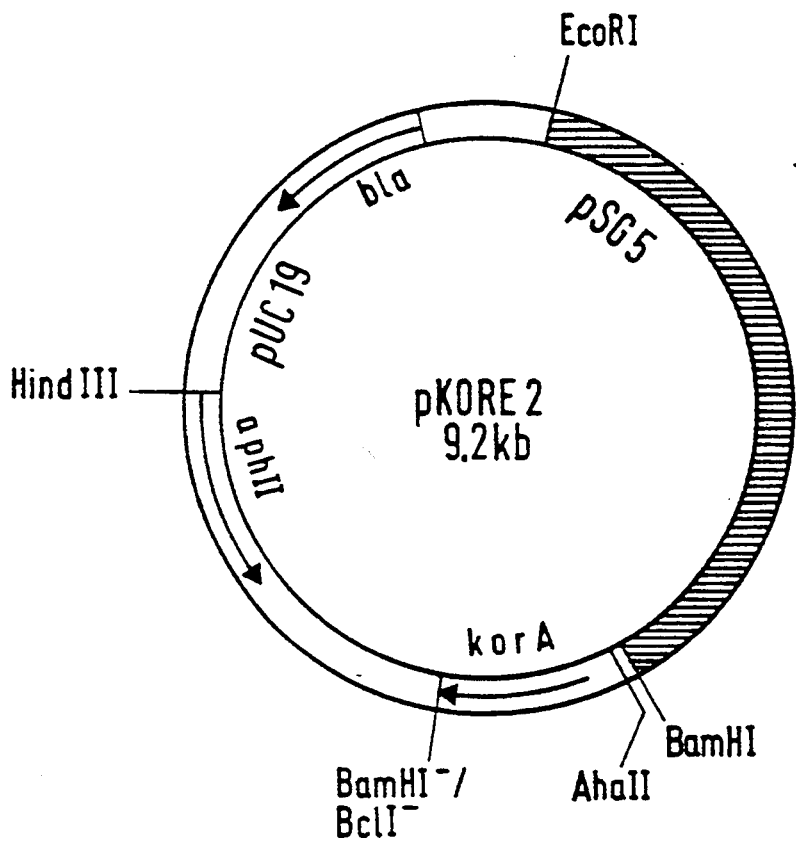
FIG. 1 is a diagram of plasmid pKORE2 containing the kor A gene and the temperature-sensitive replicon from plasmid pSG5.

It has now been found that the kil-kor system, which is known per se, from the plasmid pIJ101 can be utilized for regulated gene expression in Streptomycetes. This system has been described by Kendall and Cohen, J. Bacteriol. 169 (1987) 4177–4183; 170 (1988) 4634–4651, and the complete nucleotide sequence of the plasmid pIJ101 is depicted in the second reference mentioned. Reference is made to this sequence hereinafter. It has been found, in particular, that the regulatory region of the kilA gene is particularly well suited for the process according to the invention.

The invention thus relates to a process for the regulated expression of a gene in a Streptomycetes host strain, in which process the kilA-KorA system is utilized as a switch, where the gene to be expressed is coupled to the kilA regulatory region, and the KorA protein is inactivated or eliminated to switch on. Further developments and preferred embodiments of this invention are explained in detail hereinafter and defined in the patent claims.

DESCRIPTION OF THE PREFERRED EMBODIMENTS

One part of the "switch" according to the invention exists in the regulatory region of the kilA gene, by which is meant that DNA region which is repressed by attachment or binding of the KorA protein and which expediently, but not necessarily, embraces the promoter of the kilA gene. This region is bounded in the natural DNA sequence by the cleavage sites of the enzyme BglII (starting at nucleotide No. 6160) or HinfI (starting at nucleotide No. 6027) and NcoI (starting at nucleotide No. 5764), with the last-mentioned cleavage site also including the ATG start codon of the KilA protein (called tra therein). The DNA sequence TTGACA of the −35 region of the kilA promoter starts with nucleotide No. 5975, and transcription starts at nucleotide No. 5939. Knowing these data it is possible to use shorter or modified DNA segments for the regulatory region and, where appropriate, to employ another promoter.

The gene to be expressed in a regulated way can be ligated directly onto the protruding sequence corresponding to the NcoI cleavage site. The NcoI cleavage site can be retained if the first codon after the start begins with G.

The second essential component of the "switch" according to the invention is the KorA protein, which acts as repressor for the kilA gene. As long as adequate amounts of active KorA protein are present, regulated expression of the required gene is switched off. There are thus two possibilities in principle for the switching on:

a) The KorA protein is inactivated or
b) it is eliminated.

The KorA protein can be inactivated by expressing a temperature-sensitive mutant of this protein and, in order to switch on the required gene, raising the temperature above the threshold above which the temperature-sensitive mutant becomes inactive, i.e. is no longer suitable for repression of the regulatory region of the kilA gene. The preparation of such temperature-sensitive mutants is known and described, for example, by Birch et al., J. Gen. Microbiol. 131 (1985) 1299–1303. Mutations of this type take place in high yield, and the resulting temperature-sensitive proteins are easy to find using an appropriate assay within the scope of the present invention.

The KorA protein can be eliminated by several processes:

It is possible to bring the korA gene under the control of a switchable promoter. It is known that the transcription of an mRNA for a lysine decarboxylase is repressed by addition of iron(III) chloride to the culture (Schupp et al., Gene 64 (1988) 179–188). Addition of heavy metal ions to an industrial fermentation batch may, however, be disadvantageous, for example because of the risk of corrosion associated therewith.

It is more advantageous to integrate the korA gene into a temperature-sensitive plasmid, in which case use can be made of its own promoter or of another promoter active in Streptomycetes. Temperature-sensitive plasmids replicating in Streptomycetes are known and described, for example, by Birch et al. However, plasmids which make use of the temperature-sensitive replicon of the plasmid pSG5 are particularly advantageous. This plasmid is described in EP-B 0 158 872 and in U.S. Pat. No. 4,880,746, and the use of pSG5 as temperature-sensitive plasmid is described in EP-A 0 334 282. The plasmid pSG5 has a wide host range and is compatible with a number of other Streptomycetes plasmids. EP-B 0 158 201 describes shuttle vectors which make use of these properties.

It is therefore possible and particularly advantageous according to the invention to incorporate the korA gene into a plasmid which contains the temperature-sensitive replicon of pSG5, in which case the gene to be expressed is incorporated under the control of the kilA regulatory region into another plasmid which is compatible with the pSG5 derivative and still undergoes stable replication above the threshold temperature of the pSG5 replicon.

The korA gene is expediently employed as AhaII-BclI fragment from the plasmid pIJ101 (the recognition sequence for AhaII starts at nucleotide 5930, the recognition sequence of BclI starts at 6753; the CGCACA sequence of the −35 region of the korA promoter starts at nucleotide 5957, and transcription starts at nucleotide No. 5992).

If use is made of the procedure with two different plasmids, it is possible, but not necessary, for both plasmids to be shuttle vectors. However, care must be taken that the two plasmids do not contain any homologous regions in order to rule out interfering recombination processes.

The gene to be expressed can be accommodated on a customary Streptomycetes expression plasmid under the control of the KilA regulatory region. An advantageous development of the invention comprises coupling the gene which codes for the required protein and, for example, encodes proinsulin to the gene for the α-amylase inhibitor tendamistat or to a part of this gene. The fusion protein encoded thereby is ejected from the cell and can be obtained from the fermentation supernatant straightforwardly. Gene fusions of this type are described, for example, in EP-A 0 281 090 and 0 289 936, with EP-A 0 289 936 containing several examples of expression plasmids which encode fusion proteins containing proinsulin.

The invention is explained in detail in the examples which follow:

EXAMPLES

1) Construction of the vector pKORE2
The plasmid

Because of the wide host range of the pSG5 replicon and the compatibility with many other vector systems, for example based on the plasmids pSVH1 (EP-B 0 070 522, U.S. Pat. No. 4,673,642), pSG2 (EP-B 0 066 701, U.S. Pat. No. 4,621,061), pIJ101 (Kieser et al., Mol. Gen. Genet. 185 (1982) 223–238) and SLP1.2 (Thompson et al., Gene 20 (1982) 51–62), the plasmid pKORE2 can be combined with many plasmids which encode the required protein.

EXAMPLE 2

Heat-induced production of fusion proteins

The promoter region of the kilA gene of the plasmid pIJ101 is cut out with the restriction enzyme Sau3A and cloned into the unique BamHI cleavage site of the "promoter selection vector" pIJ 487 (obtainable from the John Innes Foundation). After transformation of S. lividans TK24, successful cloning events are recognized by the expression of neomycin resistance. The isolated promoter region (fragment 1) can now be cut out with the restriction enzymes KpnI and SphI and be isolated by electroelution in a known manner.

The α-AI promoter is deleted from the plasmid pGF1 (EP-A 0 289 936, ZA 88/3168, AU-A 15 559/88, NZ 222 464) by replacing an SphI-XaIII DNA fragment by the truncated synthetic SphI-XmaIII DNA fragment (SEQ ID NOS. 1,2, and 3)

```
                                              10
          (MET) ARG VAL ARG ALA LEU ARG LEU ALA ALA LEU VAL GLY ALA
                CGC GTA CGG GCA CTT CGA CTT GCG GCG CTG GTG GGT GCG
      G         TAC GCG CAT GCC CGT GAA GCT GAA CGC CGC GAC CAC CCA CGC
    (SphI)

20
              GLY ALA ALA LEU ALA LEU SER PRO LEU (ALA) (ALA) (SEQ ID NO: 3)
              GGC GCC GCA CTC GCC CTG TCT CCC CTC GC (SEQ ID NO: 1)
              CCG CGG CGT GAG CGG GAC AGA GGG GAG CGC CGG (SEQ ID NO: 2)
                                                       (XmaIII)
``` pIJ101 (obtainable from the John Innes Foundation, Norwich, England) is digested with AhaII and BclI, and the fragment 830 bp in size is isolated.

The EcoRI-BamHI fragment which is 3.8 kbp in size from the plasmid pSG5 (EP-B 0 158 872 and U.S. Pat. No. 4,880,746) is isolated and provided with a BamHI-AhaII linker.

The commercially available plasmid pUC19 is digested with the enzymes EcoRI and HindIII, and the large fragment which contains the bla gene is isolated.

To introduce a marker which is selectable in Streptomycetes, the HindIII-BamHI fragment which is 1.85 kbp in size and has the aphII gene from the transposon Tn5 is employed.

Ligation of these DNA fragments results in the plasmid pKORE2 which is 9.2 kbp in size (FIG. 1). It contains the temperature-sensitive replicon from the plasmid pSG5 and thus undergoes stable replication only at temperatures below 34° C. By contrast, at temperatures above 36° C., plasmid replication is inhibited and the plasmid is eliminated from the cell.

The result is the plasmid pGF1pl which contains the complete fusion construction composed of signal sequence, α-AI gene, proinsulin gene and termination sequence. This DNA sequence (fragment 2) can be cut out by digestion with the restriction enzymes SphI and SstI and be isolated in a known manner.

The commercially available expression vector pIJ702 (John Innes Foundation) is digested with the restriction enzymes KpnI and SstI, and the large fragment (fragment 3) is likewise electroeluted.

Figure 2:
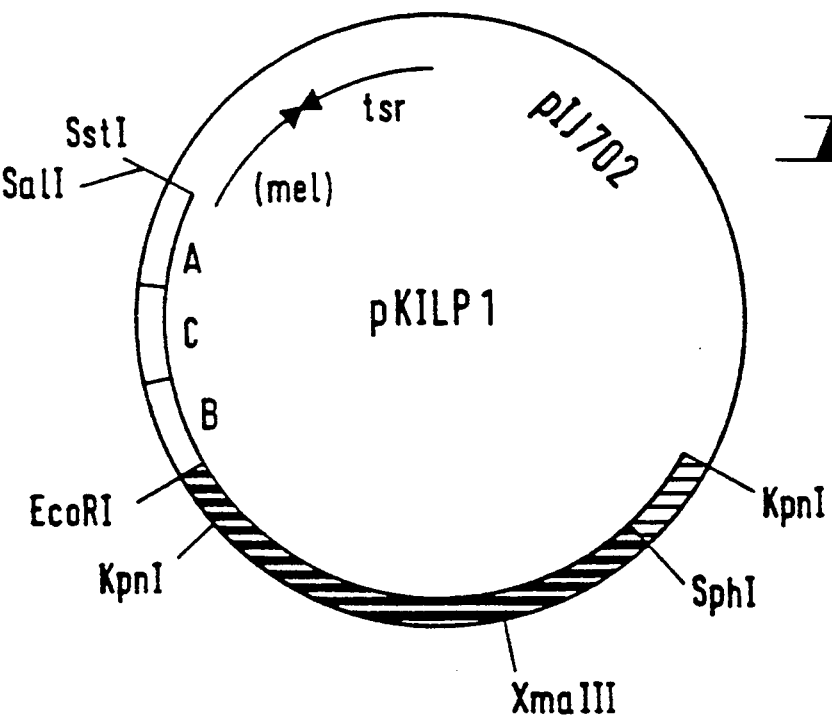
FIG. 2 is a diagram of plasmid pKILP1 containing the isolated promoter region of the kil A gene from plasmid pIJ 487, the signal sequence of the alpha-AI gene, the proinsulin gene and its termination sequence, and plasmid sequences from plasmid pIJ702.

Ligation of fragments 1, 2 and 3 results in the recombinant plasmid pKILP1 (FIG. 2). The transformation of S. lividans TK24, which already contains the compatible plasmid pKORE2, is followed by selection for the presence of the thiostrepton and neomycin resistance markers. After the temperature has been raised to 36° C., clones which contain both plasmids secrete the required fusion protein composed of the α-amylase inhibitor and proinsulin, which can be detected and isolated in a manner known per se.

---

We claim:

1. A process for the regulated expression of a gene in a Streptomycetes host strain, which comprises employing as a switch the kilA-KorA system, where the gene to be expressed is coupled to the kilA regulatory region, and is switched on by the elimination of the KorA protein when the korA gene is expressed from a plasmid with temperature-sensitive replication, and the temperature is raised above the plasmid's threshold.

\* \* \* \* \*